United States Patent [19]
Bird

[11] 4,164,219
[45] Aug. 14, 1979

[54] VENTILATOR

[75] Inventor: Forrest M. Bird, Palm Springs, Calif.

[73] Assignee: Minnesota Mining and Manufacturing Company, St. Paul, Minn.

[21] Appl. No.: 730,722

[22] Filed: Oct. 8, 1976

[51] Int. Cl.² ............................................. A61M 16/00
[52] U.S. Cl. ................................. 128/145.8; 137/510
[58] Field of Search ........................... 128/145.5–145.8, 128/147, 142 R, 142.2, 142.3, 146.5, 185, 191 R, 188, 195, 201, 203, 204, 205, 208, 209, 210, 211, 30, 28, 30.2, DIG. 17, DIG. 29; 137/510, 557; 251/65, 129

[56] References Cited

U.S. PATENT DOCUMENTS

| | | | |
|---|---|---|---|
| 1,875,511 | 9/1932 | Shivers | 251/65 |
| 2,996,071 | 8/1961 | Takaoka | 251/65 |
| 3,191,596 | 6/1965 | Bird et al. | 128/145.5 |
| 3,385,295 | 5/1968 | Beasley | 128/145.8 |
| 3,753,436 | 8/1973 | Bird et al. | 128/145.8 |
| 3,974,828 | 8/1976 | Bird | 128/145.8 |
| 4,060,078 | 11/1977 | Bird | 128/145.8 |

FOREIGN PATENT DOCUMENTS 1001060  1/1957  Fed. Rep. of Germany ............. 251/65

Primary Examiner—Henry J. Recla

[57] ABSTRACT

A ventilator which may be operated in either of two manually selected modes, including (1) a first mode in which ventilation of a patient is initiated by inhalation of the patient through a patient adapter and is terminated to allow the patient to exhale when the pressure at the patient adapter reaches a predetermined level; or (2) a second mode in which ventilation of the patient is initiated in the same manner as in the first mode, but in which apneustic hold means are activated when the pressure at the patient adapter reaches the predetermined level and maintains gas pressure and flow in the patient adapter for a short predetermined time thereafter before the patient is allowed to exhale.

5 Claims, 6 Drawing Figures

VENTILATOR

SUMMARY OF THE INVENTION

The present invention provides a ventilator having inhalation and exhalation phases in its operative cycle which may be operated in either of two manually selected modes, including (1) a first mode in which ventilation of a patient is initiated by inhalation of the patient through a patient adapter and is terminated to allow the patient to exhale when the pressure at the patient adapter reaches a predetermined level; and (2) a second mode in which ventilation of the patient is initiated in the same manner as in the first mode, but in which apneustic hold means are activated when the pressure at the patient adapter reaches the predetermined level and maintains gas pressure and flow in the patient adapter for a short predetermined time thereafter before the patient is allowed to exhale.

The ventilator according to the present invention comprises a gas inlet line adapted to be coupled to a source of gas under pressure; a patient adapter having a through opening terminating at an outlet opening adapted to communicate with a patient; and a sequencing switch assembly comprising control valve means having an inlet opening coupled to the gas inlet line, an outlet opening, and a spindle movable between open and closed positions for controlling the flow of gas between its openings, and control means including means for defining a control chamber, including a diaphragm coupled to the spindle for moving the spindle from its closed to its open position in response to gas pressure in the control chamber below a first predetermined pressure and for moving the spindle from its open to its closed position upon gas pressure in the control chamber above a second predetermined pressure which is higher than the first predetermined pressure.

Means are provided for connecting the outlet opening of the control valve means with the through opening of the patient adapter to provide a main flow of gas to the adapter, and for connecting the control chamber with the through opening of the patient adapter to communicate gas pressures in the through opening with the control chamber so that the spindle will be moved to its open position in response to gas pressure in the through opening below the first predetermined pressure as may be caused by inhalation of a patient, and will be moved to its closed position in response to gas pressure in the through opening above the second predetermined pressure as may be caused by resistance to air flow in the patient's respiratory system.

Exhalation valve means are coupled to the through opening of said patient adapter which have an operating chamber and have a portion movable from a normal open position permitting gas flow to the atmosphere from the patient adapter so that the patient can exhale through the patient adapter, to a closed position preventing gas flow to the atmosphere from the patient adapter when the gas pressure in its operating chamber is above a third predetermined pressure so that the patient can be positively ventilated through the patient adapter.

Conduit means are provided for directing a secondary flow of gas at above the third predetermined pressure to the patient adapter and to the operating chamber of the exhalation valve means, as are apneustic hold means including means for supplying gas to an outlet line from an inlet line coupled to the gas inlet line while the spindle is in its open position and for a predetermined time after the spindle is moved from its open position to its closed position, and a mode selector means including means for connecting the outlet opening of the control valve means to a first inlet of the mode selector means, means for connecting the outlet line of the apneustic hold means to a second inlet of the mode selector means, and means connecting an outlet of the mode selector means to the conduit means. The mode selector means includes a portion movable between a first position for connecting its first inlet to its outlet, and a second position connecting its second inlet to its outlet. Thus when the portion is positioned in its first position, gas is directed to the patient adapter and the exhalation valve means from the outlet opening of said control valve means to apply gas pressure at the patient adapter only when the spindle is in its open position; and when the portion of the mode selector means is positioned in its second position gas is directed to the patient adapter and the exhalation valve means from the gas inlet line via the apneustic hold means and the conduit means to apply gas pressure at the patient adapter both when the spindle is in its open position and for a predetermined time after the spindle moves to its closed position.

BRIEF DESCRIPTION OF THE DRAWING

The present invention will be further described with reference to the attached drawing wherein like numbers refer to like parts in the several views, and wherein.

DESCRIPTION OF THE PREFERRED EMBODIMENTS

Figure 1:
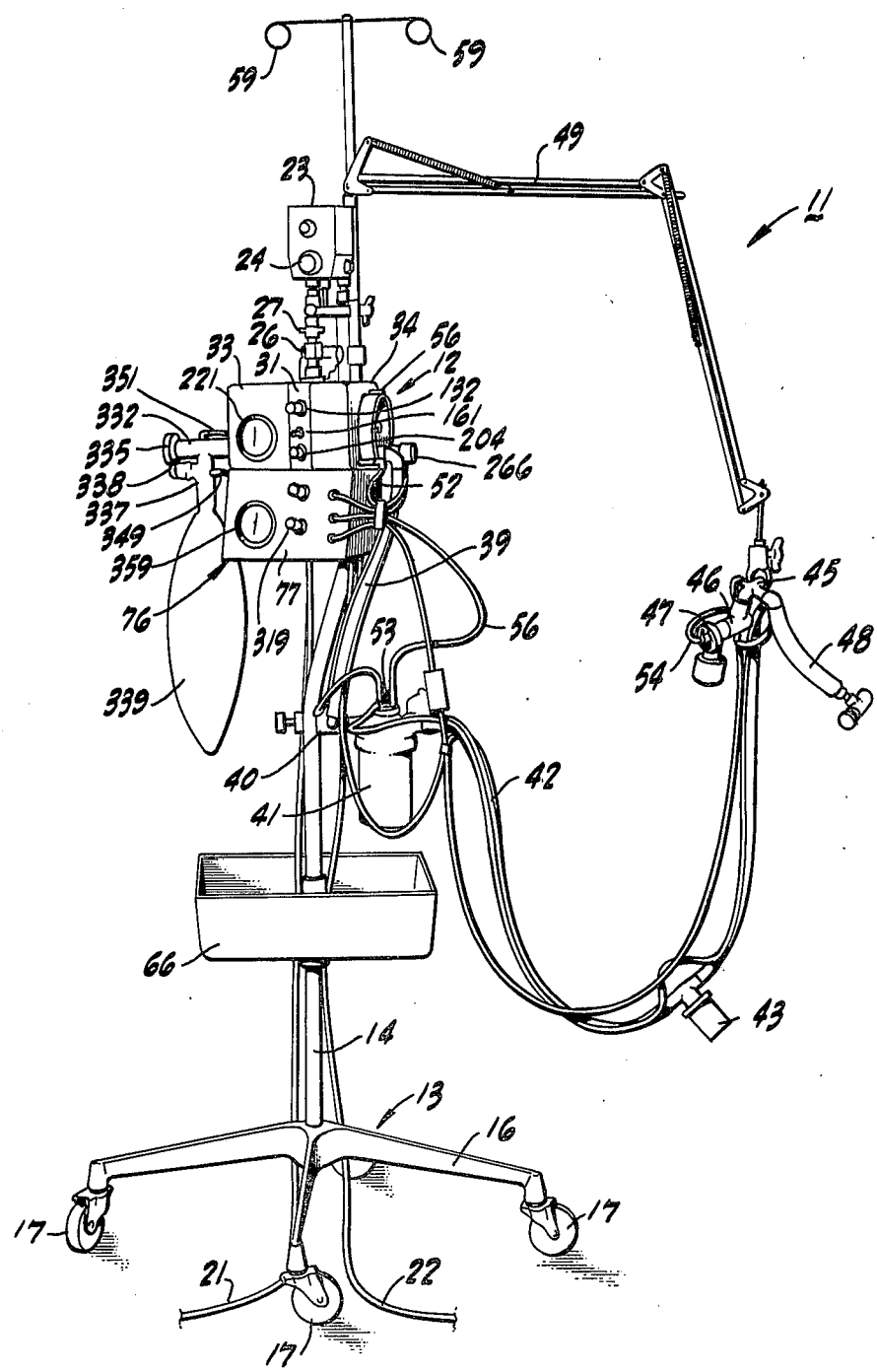
FIG. 1 is a perspective view of a ventilator incorporating the present invention with an I.M.V. Generator attached thereto.

The ventilator 11, which is shown in FIG. 1 of the drawings, consists of a control cabinet or case 12, which is carried by a stand 13. The stand 13 consists of a vertical post 14, which is carried by a four-legged base 16 which is provided with castered wheels 17 provided on the outer extremities of the base. The support post 14 as shown in the drawings is positioned so that the control cabinet or case 12 is generally centered over the lower extremity of the support post 14. The cabinet or case 12 is provided with a clamp (not shown) for securing the cabinet or case to the post 14.

A suitable source of gas is provided for the control cabinet or case 12 such as a supply of oxygen under pressure and a supply of air under pressure. The oxygen and the air are supplied through hoses 21 and 22 and are connected to an oxygen blender 23 of the type described in U.S. Pat. No. 3,727,627. The blender is provided with a control knob 24 by which the percent of oxygen which is supplied to the control cabinet or case 12 can be adjusted. The oxygen blender 23 is connected to a fitting 26 provided on the cabinet or case 12 which is connected to the oxygen blender by a wing nut 27.

The control cabinet or case 12 consists of a main or control body 31 formed of a suitable material such as aluminum. A pair of end members or compartments 33 and 34 are secured to the control body 31 and are formed of a suitable material such as transparent plastic. The end member 33 in conjunction with the control body 31 defines an ambient compartment 36 which serves as a housing for mechanical components as hereinafter described as well as a source for ambient entrainment of air to be utilized in the ventilator. The end member 34 in conjunction with the control body 31 forms a pressure compartment 37 which serves as a type of plenum chamber for the delivery of respiratory gases.

The pressure compartment 37 is provided with a breathing outlet 38 in the end member 34 which is connected to a large flexible hose 39. The hose 39 is connected to a fitting 40 carried by the post 14 and which has a passage (not shown) in communication with the inlet of a large nebulizer 41 of the type described in U.S. Pat. No. 3,353,356. The large nebulizer 41 is carried by the fitting 40 and has an outlet which is connected to a large tube 42. The tube 42 is connected to one end of a conventional water trap 43. The other end of the water trap 43 is connected by a large tube 44 to one leg of a wye 45. The other leg of the wye 45 has a tee shaped member 46 mounted thereon. An exhalation valve assembly 47 is mounted on the member 46 is blocked off by an insert (not shown). The remaining leg of the wye 45 is connected to a patient adapter such as a tracheotomy fitting 48. The wye 45 is adapted to be carried by a parallelogram assembly 49 carried by the post 14.

The end member 34 is provided with an inspiratory power or service socket 51 connected to a small tube 52. The tube 52 is connected to a tee 53 mounted on one of the jets of the nebulizer 41. The tee 53 is also connected by a tube 54 to the exhalation valve assembly 47. The end member 34 is also provided with an expiratory power or service socket 56 to supply gas during the exhalation phase for powering other devices such as a pneumatic belt as described in U.S. Pat. No. 3,454,000.

An IV hanger 59 is carried by the post 14. A tray 66 is also carried by the stand 13. An inlet filter 69 is provided for the ambient department and is mounted in a manner hereinafter described. An intermittent mandatory ventilation generator 76 hereinafter called an I.M.V. Generator is mounted in a cabinet 77 secured to the bottom of the ventilator 11.

The control cabinet or case 12 is in many respects similar to the control cabinet disclosed in U.S. Pat. No. 3,234,932 and includes a number of similar parts. For this reason the mechanical construction of the control cabinet 12 and all the components mounted therein will not be described in detail. Rather, they will be described in conjunction with a schematic diagram which is shown in FIG. 2.

Source gas is obtained from the lines 21 and 22 connected to the oxygen blender 23 and is supplied to the inlet stem or fitting 26 of the ventilator through a plastic filter element 82 and into a passage 83 provided in the control body 31. The passage 83 is in communication with a passage 84 which is in communication with the inlet of the expiratory termination cartridge 86. The passage 83 is also in communication with a passage 87 which is in communication with the inlet of the expiratory flow cartridge 88. Passage 83 is also in communication with the passage 89 in the control body 31. The passage 89 is in communication with a line 90, which is in communication with the inlet of the apneustic hold cartridge 91. Conduit 83 is also in communication with another passage 92 and the passage 92 is in communication with the line 95 which is in communication with the inlet of a flow accelerator cartridge 93. The conduit 83 is also in communication with the inlet of a sequencing switch 94. The sequencing switch 94 consists of a spool 96 which is provided with an inlet 97 and an outlet 98. Flow between the inlet and outlet 98 is controlled by a sliding spindle 99. Full travel of the spindle 99 to the right permits internal communication between the inlet 97 and the outlet 98, which is the "on" position for the sequencing switch. Flow is completely interrupted when the spindle travels full left to the "off" position. A central shaft 100 serves to retain the spindle within the spool 96. The left end of the shaft 101 is connected to a master diaphragm 101 which is utilized for servoing the spindle 99 on and off. The opposite ends of the central shaft carry armature discs or plates 102. The armature plates 102 are attracted by magnets 103 carried by adjustable shafts 104 threaded into the respective end compartments 33 and 34 to provide latch levers 106 and 107 with the latch lever 106 being the inspiratory starting effort latch lever and latch lever 107 being the inspiratory pressure limiting latch lever. The permanent magnet 103 carried by the latch lever is association with the armature plate 102 forms a magnetic clutch which makes it possible to adjust the starting effort and the inspiratory pressure limit. It can be seen that the spindle 99 is captured between two magnetic clutches and is either completely "on" with the pressure clutch (the left hand clutch) engaged, or completely off with the sensitivity clutch (the right hand clutch) engaged.

Figure 2:
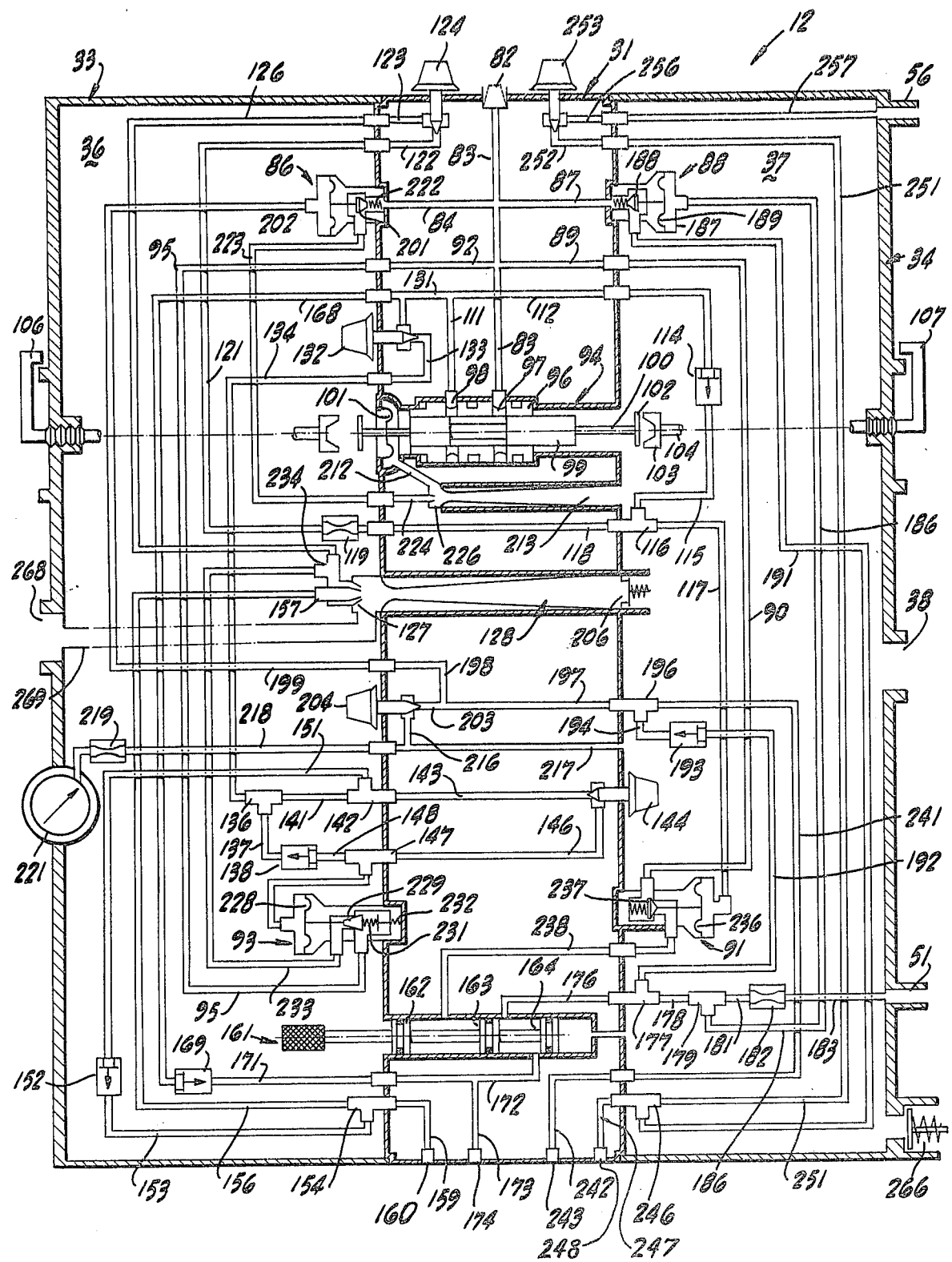
FIG. 2 is a schematic diagram of the ventilator as shown in FIG. 1.

Let it be assumed that the spindle or shuttle valve 99 has been moved to the right to the "on" position as viewed in FIG. 2 to initiate the inspiratory phase. When this occurs, source gas will be delivered from the passage 83 through the sequencing switch 94 to a passage 111 where it is supplied to a passage 112, through an apneustic timing check valve 114, line 115, tee 116, a line 117 to the diaphragm side of the apneustic hold cartridge 91. The tee 116 is also connected by passage 118 to an orifice 119 of a suitable size as, for example, 0.013 of an inch which meters gas at a controlled rate from the diaphragm side of the apneustic hold cartridge. This bleed down gas is supplied from the orifice 119 through a conduit 121. The conduit 121 is connected to a passage 122 in the control body 31. The passage 122 is in communication with another passage 123 in the control body. The rate of flow from the passage 122 to the passage 123 is controlled by an apneustic flow time valve assembly 124. The passage 123 is connected to a line 126. From the foregoing it can be seen that the gas is limited before it arrives at the apneustic flow time valve assembly 124 by the orifice 119. The gas passing through the apneustic flow time valve assembly 124 is dumped into the master small Venturi assembly 128 through the dual jets 127 so that the inspiratory gas dumped into the system is not wasted.

Inspiratory gas also is supplied from the conduit 111 through a conduit 131 to an inspiratory flow rate control valve assembly 132 which is mounted in the control body 31. This controls the flow of gas from the conduit 131 to a conduit 133 provided in the control body. The conduit 133 is connected to a tube 134. Tube 134 is connected to one leg of a tee 136. Another leg of the tee 136 is connected by a tube 137 to a flow acceleration reset check valve assembly 138. Another leg of the tee 136 is connected by a tube 141 to a leg of another tee 142. The tee 142 is mounted on the control body 31 and is in communication with a passage 143 leading to an expiratory flow acceleration slope control valve assembly 144. The valve assembly 144 supplies gas to conduit 146 provided in the control body 31 and which supplies it to a tee 147. One leg of the tee 147 is connected by a tube 148 to the other side of the flow accelerator reset check valve assembly 138. Another leg of the tee 147 is connected by a tube 148 to the diagraphm side of the flow accelerator cartridge 93. Thus, it can be seen that the inspiratory gas is supplied to the flow accelerator reset check valve assembly 138 to hold it competent during the inspiratory phase. This inspiratory gas is also supplied from one leg of the 142 through a tube 151 to one side of the check valve assembly 152. The other side of the check valve assembly 152 is connected by a tube 153 to one leg of a tee 154. Another leg of the tee 154 is connected by a tube 156 to the center jet 157 of the master small Venturi assembly 128.

Inspiratory gas is also supplied from the tee 154 mounted in the control body 31 to a passage or conduit 159 provided in the control body 31 and terminating in a port 160. The port 160 can be identified with the designation "accessory augmented I.M.V. inlet gas or metered inspiratory flow".

The letters IMV stand for intermittent mandatory ventilation. When the intermittent mandatory ventilation is not used, the outlet port 160 is capped.

A mode selector switch 161 is provided in the control body 31 and is movable between two positions which are characterized herein as in and out positions. When the mode selector switch 161 is pulled to its out position illustrated in FIG. 2, it causes operation of the ventilator in a first mode in which ventilation of a patient can be initiated by inhalation of the patient through a patient adapter and is terminated to allow the patient to exhale when the pressure at the patient adapter reaches a predetermined level; and when it is pushed to its in position (not illustrated), it causes operation of the ventilator in a second mode in which ventilation of the patient is initiated in the same manner as in the first mode, but in which apneustic hold means are activated when the pressure at the patient adapter reaches the predetermined level and maintains gas pressure and flow in the patient adapter for a predetermined time thereafter before the patient is allowed to exhale. The mode selector switch 161 is provided with lands 162, 163 and 164, which cooperate with a cylinder 166 provided in the control body 31.

As hereinbefore explained, inspiratory gas supplied to the conduit 131 provided in the control body 31 and is supplied from the conduit 131 through a tube 168 and then through an apneustic flow check valve assembly 169 and thence through another tube 171 which is in communication with a conduit 172 provided in the control body 31. Gas is delivered from conduit 172 to the mode selector switch 161 between the lands 163 and 164 when the mode selector switch 161 is out to cause operation of the ventilator in its first mode. Another conduit 173 is provided in the control body 31 in communication with the conduit 172 and serves to provide accessory inspiratory gas port or outlet 174. Gas is supplied from between the lands 163 and 164 through a conduit 176 in communication with the mode selector switch 161 to a tee 177 which is mounted on the control body 31. The tee 177 is connected by line 178 to another tee 179. The tee 179 is connected by line 181 to an orifice 182. The orifice 182 is connected to a line 183 which is connected to the inspiratory service socket 51 provided on the end member 34.

Inspiratory gas is also supplied from the tee 179 through a line 186 to pressurize the diaphragm side of an expiratory flow cartridge 187 to move its valve member 188 to a closed position. Thus, it can be seen that as soon as the diaphragm 189 is pressurized, expiratory flow of gas through the line 191 is terminated.

Inspiratory gas is supplied from the tee 177 through a line 192 to an expiratory termination reset valve 193 and thence through a line 194 to a tee 196 mounted on the control body 31. The tee 196 is in communication with a passage 197 provided in the control body. The passage 197 is in communication with a passage 198 which is connected to a tube 199. The tube 199 is connected to the diaphragm side of the expiratory termination cartridge 86 which is provided with a valve member 201 and a diaphragm 202 which when gas is supplied to the expiratory termination cartridge 86, moves the valve member 201 to a closed position. Inspiratory gas is also supplied from the line 197 to a line 203 to a controlled expiratory time valve assembly 204.

As pointed out above, during the expiratory phase gas will flow from the master venturi 128 through the distal venturi gate 206. The gate 206 prevents reverse flow through the master venturi 128. This gas is supplied to the pressure compartment 37 in end member 34 which is provided with a breathing circuit outlet port 38. The gas from the outlet port 38 is supplied through the large tube 39 through the large nebulizer 41 and thence through tube 42, water trap 43, tube 44, to the patient adapter 48, and to the lungs of the patient. The exhalation valve assembly 47 is maintained in a closed position by gas being supplied from the inspiratory service socket 51 and through the tubes 52 and 54 to the exhalation valve assembly 47 to maintain it in a closed position. Gas supplied to the patient adapter 48 during the inspiratory flow is from two sources. One is from the center jet 157 of the master venturi 128 and the second is from the jet of the nebulizer 41.

As pressure in the inspiratory circuit increases, this pressure is applied to the master diaphragm 101 of the sequencing or servo switch assembly 94. It should be noted that the other side of the master diaphragm 101 is vented by a passage 212 in the control body 31 to a sensing/servoing venturi 213 which opens into the pressure compartment 37. When there is sufficient pressure in the pressure compartment 37, the master diaphragm 101 is urged to the left as shown in FIG. 2 to move the sequencing switch 94 to the off position.

When sequencing switch 94 has been moved to the off position, the communication between the inlet passage 83 and the outlet 111 is interrupted to prevent further flow of source gas and to thereby terminate the inspiratory phase.

Upon termination of the inspiratory phase, loading of the expiratory termination cartridge 86 ceases and there is a gradual bleed down of gases from the diaphragm side of the cartridge through the line 199, passage 198, passage 203 through the controlled expiratory time valve assembly 204 and then through passages 216 and 217 provided in the control body 31. The passage 217 opens into the pressure compartment 37. It is also connected by a line 218 through an orifice 219 to an airway pressure manometer 221. The orifice 219 serves to dampen the pressure fluctuations to the manometer 221.

As soon as the gas behind the diaphragm 202 of the expiratory termination cartridge 86 has been bled off sufficiently, the valve member 201 will be moved to an open position by a spring 222 to permit gas to be supplied from the passage 84 through a line 223 which is connected to a passage 224 provided in the control body 31. The passage 224 is connected into a center jet 226 in the sensing/servoing venturi 231 which opens into the pressure compartment 37. It can be appreciated that the greater the pressure drop which occurs across the center jet 226 of the sensing/servoing venturi 213, the greater the pressure on the distal end of the venturi 213 which can be overcome and still transmit the same pressure to the master diaphragm 101 to cause the sequencing 94 to be switched or to commence the inspiratory phase.

When the flow acceleration is desired during the inspiratory phase, the inspiratory flow rate control valve 132 is opened up to permit relatively rapid flow of inspiratory gas from line 131 through the line 133, line 134, tee 136, line 141, tee 142, passage 143 to the flow acceleration slope control valve assembly 144. the slope control valve assembly 144 meters the gas into passage 146 and supplies it to the diaphragm side of the flow accelerator cartridge 93, thus bypassing the flow accelerator reset check valve 138 which allows any remaining pressure in the diaphragm side of the flow accelerator cartridge 93 to be quickly released through lines 148, 137, 141, 151, 153, 156, and master venturi center inlet jet 157 when the sequencing switch is moved from its on to its off position. The rate at which the flow accelerator cartridge 93 will be activated will be controlled by two factors. One is the size of the opening provided by the inspiratory flow rate control valve assembly 132 and the other is the opening provided by the flow acceleration slope control valve assembly 144. The more gas that passes into the line 146, the faster a given pressure will be established in the flow accelerator cartridge 93 to cause the diaphragm 228 to be moved to the right as viewed in FIG. 2 to open the valve member 229 against the force of the spring 231. As soon as the flow accelerator cartridge 93 is opened, inspiratory gas is supplied from the passage 83 through the passage 92 through the line 95 through the flow accelerator cartridge 93 and then through a line 233 to a tee 234 to the dual jets 127 of the master venturi 128. Also it should be pointed out that excess gas from the apneustic flow time control valve assembly 124 is supplied through the line 126 to the tee 234.

By adjustment of the flow acceleration slope control valve assembly 144, it is possible to obtain great variations in the time before flow acceleration is provided. With the flow acceleration control assembly 144 in a wide open position, it is possible to obtain almost instantaneous flow acceleration with flows well over 300 liters per minute. The flow accelerator cartridge 93 is provided with the means for adjusting the force on the valve member 229. First there is a piston affect supplied by the gases in line 95 to the other side of the valve member 229. In addition, there is the yieldable force of the spring 231. The force which the spring 231 applies to the valve member 229 can be adjusted by means of a screw 232. By the use of the screw 232 it is possible to calibrate the flow accelerator cartridge 93.

The inspiratory phase continues until sufficient pressure is built up in the pressure compartment to cause the master diaphragm 101 to move to the left as viewed in FIG. 2 to terminate the inspiratory phase. Thus, there is no longer inspiratory gas passing through the inspiratory timing circuitry which includes the gas behind the diaphragm 228 of the flow accelerator cartridge 93 is emptied through line 148, the flow accelerator reset check valve 138, line 137, tee 136, line 141, line 151, accessory IMV check valve 152, line 153, tee 154, line 156 and through the center jet 157 of the master venturi 138 and into the pressure compartment 37 and out through the breathing outlet port 38.

Now let it be assumed that the selector switch 161 is pushed in to cause operation of the ventilator in its second mode instead of in its first mode. If this is done when the ventilator is in operation, it will not affect the phase that the ventilator is in. Inspiratory gas is delivered from the passage 83 through the passage 89 thence through the line 90 to the inlet side of the apneustic hold cartridge 91. At the same time, inspiratory gas is supplied from the conduit or passage 83 through the sequencing switch 94 through the passage 111, passage 112, line 113, apneustic timing check valve 114, line 115, tee 116, line 117 to the diaphragm side of the apneustic hold cartridge 91.

This inspiratory gas applied pressure to the diaphragm 236 to move the valve member 237 to an open position to permit inspiratory gas to flow into a line 238 and into the mode selector 161 between the lands 162 and 163. As explained above, when the mode selector 161 is pulled out, nothing occurs because of the inspiratory gas delivered through the line 238. However, when the mode selector 161 is pushed in, this inspiratory gas is delivered to passage 176 and then through tee 177, line 178, tee 179, line 181, orifice 182 and line 183 to the inspiratory service socket 51. Gas is also delivered from the tee 179 through the line 186 to pressurize the diaphragm side of the expiratory flow cartridge 88 and therefore loads the inspiratory termination circuit. At the same time gas is supplied from the tee 177 through line 192, the expiratory termination reset valve 193, line 194, tee 196, passage 197, passage 198 to line 199 to the pressure side of the expiratory termination cartridge 86. Thus it can be seen that when the mode selector 161 is pushed in to cause operation of the ventilator in its second mode, both the expiratory flow cartridge 88 and the expiratory termination cartridge 86 are loaded to keep these normally open cartridges closed.

From when the selector switch 161 is in to cause operation of the ventilator in its second mode; foregoing it can be seen that the loading of the expiratory flow cartridge 88 and the expiratory termination cartridge 86, is accomplished via gas passing through the mode selector 161; whereas when the mode selector is out to cause operation of the ventilator in its first mode, such loading is accomplished by supplying inspiratory gases from the passage 83 through the sequencing switch 94, passage 111, passage 131, line 168, apneustic flow check valve 169, line 171, line 172 and thence through the line 176, and the tees 177, 179 to pressurize the expiratory flow cartridge 88 and the expiratory terminatin cartridge 86, in the same manner as hereinbefore described. When the mode selector 161 is pushed in to cause operation of the ventilator in its second mode, however the passage 172 is isolated and is out of communication with the passage 176.

When the sequencing switch 94 is in the off position, and the mode selector switch 161 is pushed "in" to cause operation of the ventilator in its second mode, apneustic flow of gases continues because the diaphragm 236 is pressurized to keep the valve member 237 in an open position in the apneustic hold cartridge 91 so that there is a continuous flow from the passage 83, through line 90, through the apneustic hold cartridge 91 and then through the line 238, through the mode selector 161, through line 176, tee 177, line 192 expiratory termination reset valve 193, line 194, tee 196 and then through line 241 through passage 242 in the control body 31 and out through a fitting or port 243, which can carry the identification "accessory apneustic flow and expiratory time extension". Apneustic flow continues until there is a bleed down of the pressure behind the diaphragm 236 to permit the valve member 237 to move to a closed position. The time required for this bleed down is controlled by the apneustic flow time valve assembly 124. The bleed down of gas from behind the diaphragm passes through the line 117, tee 116, passage 118, orifice 119, line 121 to passage 122 past the apneustic flow time valve assembly 124, through the passage 123, line 126, tee 234 and through the dual jets 127 of the master venturi into the pressure compartment 37. The apneustic flow valve assembly 124 is normally adjusted so as to provide apneustic flow times ranging from 0 to 3 seconds.

It can be seen that apneustic flow is only provided when the mode selector switch is in to cause operation of the ventilator in its first mode because when the mode selector switch 161 is "out" to cause operation of the ventilator in its second mode the passage 238 is dead headed into the selector switch 161.

After termination of the inspiratory phase, with the ventilator either in its first or its second mode, air under pressure is no longer supplied to the passage 176 through tee 177, tee 179, line 186 to the rear side of the diaphragm 189 of the expiratory flow cartridge 88. In addition, the line 186 is vented to the atmosphere through the tee 179 and through the inspiratory service socket 51 which is vented to the atmosphere through the exhalation valve assembly 47. As soon as the expiratory flow cartridge 88 opens after the gases have been drained off from behind the diaphragm 189, inlet gas flows from the passage 83 through the passage 87, through the expiratory flow cartridge 88, through line 191, tee 246, line 251 to the passage 252 in the control body 31, through the expiratory flow control valve 253, then through the passage 256, line 257 and out the expiratory flow service socket 56 provided in the end member 34. In addition, the inlet gas at the same time is supplied through the port or fitting 248 carrying the identification "accessory expiratory gas" which will serve an important function in connection with IMV generator hereinafter described. Thus, it can be seen that the expiratory flow cartridge 88 not only provides metered gas for the expiratory flow service socket 56, but also provides unmetered gas to the accessory expiratory gas port 248 during the mechanical expiratory phase of the ventilator to perform other functions as, for example, servoing the IMV generator.

Expiratory gases continue to flow from the expiratory flow service socket 56 and from the port 248 until the expiratory phase is terminated by the operation of the expiratory termination cartridge 86. As explained previously during the expiratory phase, gas is supplied through the passage 176 or the mode selector 161, thence up through line 192, the expiratory termination reset valve 193, line 194, tee 196, passage 197, passage 198, to pressurize the diaphragm 202 and to maintain it in a normally closed position during the inspiratory phase. As soon as the inspiratory phase is interminated as hereinbefore described and an exhalation phase commences, there is a bleed-off of the gas from behind the diaphragm 202 of the expiratory termination cartridge 86 through the line 199, the passage 198, through the controlled expiratory time valve 204, through the passage 216, and passage 217 in the control body 31 and thence into the pressure compartment 37 which is open to the atmosphere through the breathing outlet port 207 and the exhalation valve 47. The rate of depressurization of the area behind the diaphragm 202 is determined by the setting of the controlled expiratory time valve assembly 204. It can be seen that the passage 197 is connected to the controlled expiratory time valve 204 and that this passage is connected by the tee 196 and line 241 to passage 242 which is connected to the port 243 identified as the "accessory apneustic flow and expiratory time extension". It can be readily seen as hereinafter described that if additional gas is supplied to the port 243 that this additional gas will augment the gas being supplied from the diaphragm 202 of the expiratory termination cartridge 86 to increase the length of the expiratory phase.

As soon as the pressure behind the diaphragm 202 in the expiratory termination cartridge 86 has been bled down sufficiently so that the valve member 201 is moved to an open position, inspiratory gas is permitted to flow from passage 83, passage 84, through the expiratory termination cartridge 86, through the line 223, passage 224, into the sensing servoing venturi 213 which will cause the sequencing switch 94 to sequence or shift to the "on" position to terminate the expiratory phase and to initiate the inspiratory phase.

The port 174 provided in the control body and carrying the identificatin "accessory inspiratory gas" is used for receiving inspiratory gas which, for example, can be supplied from the IMV generator hereinafter described. If such inspiratory gas is supplied through the line 172, it is supplied to the line 176 in the event that the mode selector 161 is pulled out to cause operation of the ventilator in its first mode. Gas entering line 171, from the line 172 is blocked by the apneustic flow check valve 169.

Gas supplied through the port 160 carrying the identification "accessory augmented IMV inlet gas or metered inspiratory flow" is supplied through the line 157, tee 154 and line 153 against the accessory IMV check valve 152. In addition, such gas flows from the tee 154 through the line 156 into the center jet 157 of the master venturi 128. As hereinafter explained, this is utilized for delivering a spontaneous IMV flow on demand during an IMV procedure.

The ventilator also includes an over-pressure governor 266 which is provided in the end member 34. Such an over-pressure governor would be set to open at approximately 65 centimeters of water pressure for general ventilatory therapy. However, when IMV procedures are utilized as hereinafter described, the over-pressure governor 266 is set so that it will not open until a pressure of 110 centimeters of water have been reached.

An entrainment port filter socket 268 has been provided in the end member 33. This socket 268 is in direct communication through a tube 269 with the master venturi 128.

"I.M.V. GENERATOR"

Figure 3:
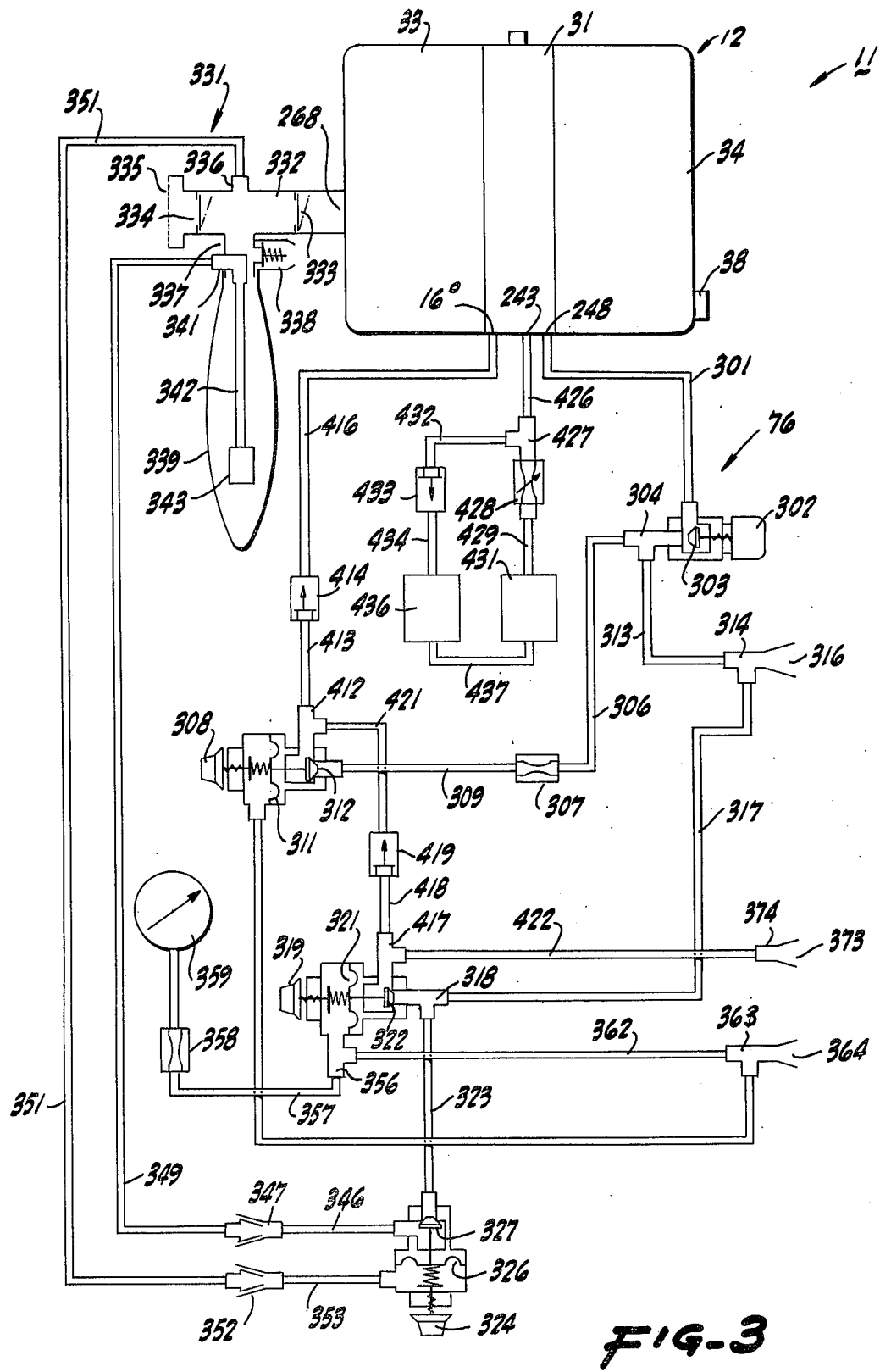
FIG. 3 is a schematic diagram of the I.M.V. Generator shown in FIG. 1.
Figure 4:
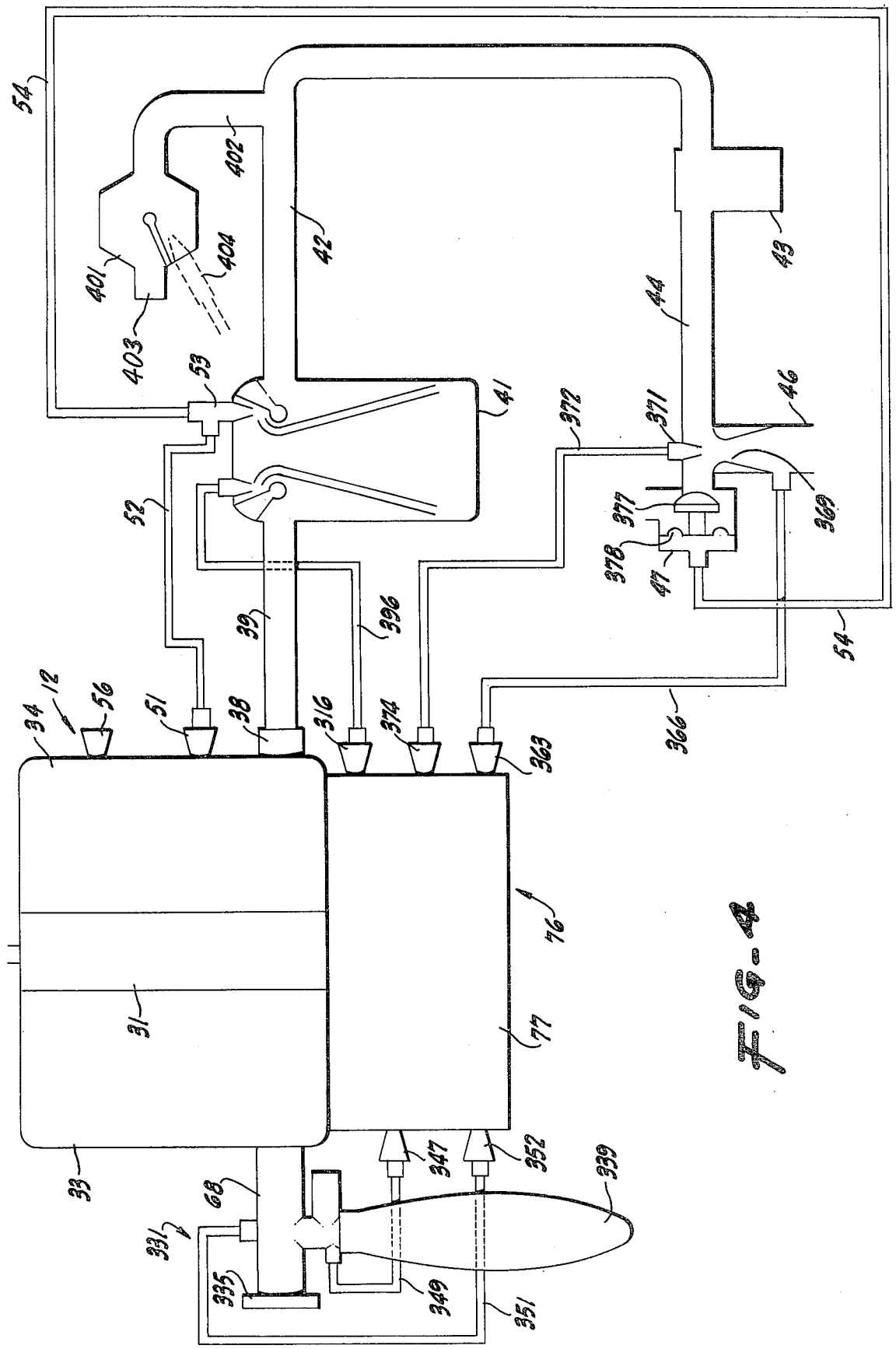
FIG. 4 is a schematic diagram of the breathing circuit utilized with the Bird ventilator and the I.M.V. Generator.

A schematic illustration of the I.M.V. Generator is shown in FIG. 3 and the schematic illustration of the breathing circuit used in conjunction with the I.M.V. Generator 76 and the ventilator 11 is shown in FIG. 4.

As pointed out previously, the I.M.V. Generator 76 includes a cabinet 77. When the I.M.V. Generator is not utilized with the ventilator as shown in FIG. 2, the ports 160, 174, 243 and 248 are plugged. When the I.M.V. Generator is to be utilized, the plugs are removed from the ports 160, 174, 243 and 248 and the cabinet 77 is secured to the bottom of the control body 31 by the use of flanged nuts (not shown) with outlet ends mounted in the ports 160, 174, 243 and 248. However, as can be seen in the I.M.V. Generator shown in FIG. 3, only three of the ports, namely ports 160, 243 and 248, are utilized.

The principal port which is utilized is the port 248 which in the I.M.V. Generator, is connected by line 301 to the inlet of an I.M.V. generator rotary master on/off switch assembly 302. The switch assembly 302 is provided with a valve member 303 for controlling the flow of gas through the switch. A tee 304 is carried by the switch 302 and has one end connected to a line 306. The line 306 is connected to a balance orifice 307 and the balance orifice 307 is connected to the inlet of a demand flow accelerator 308 by line 309. The demand flow accelerator 308 is provided with a diaphragm 311 and a valve member 312. Another leg of the tee 304 on the switch 302 is connected by line 313 to a tee 314. One leg of the tee 314 is connected to an outlet port 316 carrying the identification "auxiliary nebulizer". Another leg of the tee 314 is connected by line 317 to a tee 318. The tee 318 is carried by a baseline compensator 319 which is provided with a diaphragm 321 and a valve member 322. As shown, it can be seen that one leg of the tee 318 is connected into the inlet of the baseline compensator 319. Another leg of the tee 318 is connected by a line 323 to the inlet of a reservoir refill servo 324. The reservoir refill servo 324 is provided with a diaphragm 326 and a valve member 327. As thus far described, this represents the distribution on the source gas from the ventilator into the I.M.V. Generator through the expiratory circuit during the mechanical expiratory phase of the ventilator.

An entrainment reservoir assembly 331 is mounted in the entrainment port filter socket 268 of the ventilator as shown in FIGS. 1 and 3 for use with the I.M.V. Generator and consists of a manifold 332 which has provided therein a proximal venturi gate 333 of a flapper valve type. This proximal venturi gate 333 serves to provide a more constant tidal volume. In other words when the master venturi 128 provided within the ventilator begins to slip, there will not be a reverse flow through the fitting 268 to ambient. Thus, the gas supplied from the jets 157 and 127 in the master venturi 128 will enter the breathing circuit through the distal venturi gate 206 provided in the master venturi 128. At the other end of the manifold 332, there is provided another one-way flapper type valve 334 to permit entrainment reservoir assembly 331 is utilized in connection with the I.M.V. Generator is mounted upon the manifold 332 to permit entrainment of ambient air. The manifold 332 is provided with a fitting 336 which is used as hereinafter described. A tee shaped member 337 is mounted upon the manifold 332 and carries an overfill relief valve assembly 338. A flexible bag 339 is also secured to the member 337 and serves as an entrainment reservoir. A fitting 341 (see FIG. 3) is mounted in the member 347 and has mounted thereon a pipe 342 which extends down into the bag 339. A muffler 343 is mounted on the end of the pipe and is disposed within the bag 339.

During the expiratory phase, source gas is supplied from the line 323 through the reservoir refill servo 324 through a line 346 to a fitting 347 provided on the case 77. The fitting 347 is in communication with a line 349 that is connected to the fitting 341 provided in the member 337 and thus gas is supplied through the pipe 342 and through the muffler 343 to the interior of the bag 339. Gas continues to fill the bag until a predetermined pressure is reached within the bag. This pressure is sensed in the manifold 332 through a line 351 connected to the fitting 336. The line 351 is connected to a fitting 352 provided on the case 77 which is in communication with a line 353 connected to the diaphragm side of the reservoir refill servo 324. It can be seen that when the desired pressure as, for example, six centimeters of water pressure is supplied to the diaphragm 326, the diaphragm 326 moves the valve member 327 to a closed position to switch off or stop further filling of the reservoir bag 339. In the event that the reservoir refill servo should fail to operate for some reason, then the filling of the bag 339 continues but the filling only will continue until a pressure sufficient to cause the overflow relief pressure valve 338 to operate as, for example, a pressure of 10 centimeters of water.

The I.M.V. Generator 76 includes means for supplying a constant positive airway pressure (CPAP) which utilizes the base line compensator 319. Let it be assumed that the base line compensator 319 has been turned to the right or a full "off" position to permit the patient to breathe gas spontaneously. As can be seen from FIG. 3, the diaphragm side of the base line compensator 321 is in communication with tee 356 carried by the base line compensator. One leg of the tee is connected by a line 357 to a manometer orifice 358 and the manometer orifice 358 is connected to an airway pressure manometer 359 mounted in the case 77 of the I.M.V. Generator by line 361. The other leg of the tee 356 is connected by a line 362 to a tee 363 carried by the cabinet 77. One leg of the tee 363 serves as a port 364 and this port is connected by a line 366 (see FIG. 4) to a fitting 367 provided on member 46. As can be seen from FIG. 4, the member 46 has a venturi 369 therein which serves as a base line venturi. The member 46 is also provided with a nozzle 371 which is adapted to supply a jet of gas through the venturi 369. The nozzle 371 is connected by a line 372 into a base line servoing port 373 provided in a fitting 374 carried by the cabinet 77.

Exhalation valve assembly 47 is mounted on one leg of the member 46 and has an exhalation valve 377 adapted to be held in a closed position by a diaphragm 378 to prevent the escape of gases from the member 368 through an outlet port 379 provided in the exhalation valve assembly 47. Means is provided for supplying gas under pressure to the diaphragm 378 and consists of the tube 54 connected as hereinbefore described to the ventilator.

If desired, additional nebulization can be supplied to the breathing tube by use of a 5 cc therapy nebulizer 401 of the type described in U.S. Pat. No. 3,172,402 by a large tube 402 which is in communication with the tube 42. The inlet 403 of the nebulizer 401 can be connected into the breathing circuit outlet port 207. The nozzle 404 which is shown in broken lines of the nebulizer 401 can be connected by a line 396 to the auxiliary nebulizer port 316 so that it will be supplied with inspiratory gases at the same time the nozzle 394 is supplied with the gas. As shown in FIG. 4, the line 396 is connected to the other jet of the large nebulizer 41.

From the construction shown in FIG. 4, it can be seen that the proximal airway of the patient is sensed and this information is supplied to the proximal airway sensing port 364 of the I.M.V. Generator through the line 366 and line 362 to the diaphragm side of the base line compensator 321 and also to the airway pressure manometer 359. This information is also supplied from the tee 363 through a line 411 to the diaphragm side of the demand flow accelerator 308.

Let it be assumed that the demand flow accelerator 308 has been set to operate at a certain pressure as, for example, a pressure below two centimeters of water. When such a pressure condition is sensed in the proximal airway of the patient, the diaphragm 311 moves to open the valve 312 and permits source gas to flow from the line 301 through the I.M.V. Generator master switch 302, line 306, orifice 307, line 309, demand flow accelerator 308, and then through a tee 412 mounted on the demand flow accelerator 308. The one leg of the tee 412 is connected to a line 413 which is connected to an inspiratory phase check valve 414. The inspiratory phase check valve 414 is connected by a line 416 to the port 160 of the ventilator 11 identified "accessory augmented I.M.V. inlet gas or metered inspiratory flow". Gas supplied to this port is supplied to the center jet 157 of the master venturi 128. Thus it can be seen that when the patient drops the pressure below the predetermined pressure as, for example, two centimeters of water, this condition will be sensed by the demand flow accelerator 308 to cause gas to be delivered to the master venturi 128. It also can be seen that a patient under demand, even during the expiratory phase, can cause the flow of gas upon demand with very little effort.

Let it be assumed that it is desired to have a constant positive airway pressure as, for example, ranging from five to ten centimeters of water pressure. To accomlish this, the knob of the base line compensator 319 is turned counterclockwise for the desired amount which reduces the pressure of the spring on the diaphragm 321 of the base line compensator. Let it also be assumed that the pressure sensed in the proximal airway of the patient is less than that of the base line provided by the base line compensator 319. When this is the case, the valve member 322 is in the open position and source gas is supplied from the master switch 302 through the line 313, tee 314, line 317, tee 318, the base line compensator 319, through a tee 417 carried by the base line compensator 319 through a line 418 connected to a base line compensator check valve 419. The base line compensator check valve 419 is connected by a line 421 to the tee 412. The gas supplied through the tee 412 will pass through the inspiratory check valve 414 and up into the ventilator 11 and through the master venturi 128 in the manner hereinbefore describe in connection with the gas supplied in the demand flow accelerator 308. Thus, it can be seen that the base line compensator 319 serves to provide a bypass loop with respect to the demand flow accelerator 308. At the same time gas is delivered to the tee 412, gas is delivered from the tee 417 through a line 422 through the fitting 374 which provides the base line servoing port 373. As shown in FIG. 4, gas delivered to the base line servoing port 373 supplies gas through the inline 372 to the base line to the nozzle 371 in the base line venturi member 46 to provide a gas under pressure against the proximal airway of the patient. This creates a positive pressure in the proximal airway against which the patient must breathe. In other words, the base line compensator provides a constant positive airway pressure.

Thus, it can be seen that the demand flow accelerator 308 is utilized to provide additional flow to the master venturi 128 where it will be humidified by passing through the humidifier 391 rather than being supplied by the base line compensator 319 to the venturi 369 which would not be humidified. By placing the bypass circuit in on demand, there has been provided increased inspiratory flow so that there is less downward base line deviation.

In connection with the foregoing description, it has been assumed that the patient has been breathing more or less spontaneously utilizing the I.M.V. Generator. Now let it be assumed that it is desired to obtain an extension of the expiratory time. This is accomplished, as can be seen from FIG. 3, by connecting a line 426 into the port 243 of the ventilator 11 labeled "Accessory Apneustic Flow And Expiratory Time Extension".

When the expiratory time circuit is loaded in the ventilator, inlet gas pressure is supplied to the port 243 and is supplied through the line 426 to a tee 427. One leg of the tee is connected to an expiratory time extension orifice 428 which is connected by a line 429 to a reservoir 431. The other leg of the tee 427 is connected by line 432 to an expiratory time extension check valve 433. The check valve 433 is connected by a line 434 to a reservoir 436. The reservoir 436 is connected to the reservoir 431 by a line 437. The orifice 428 is adjustable as shown and is set for a time which is beyond the normal time of the expiratory circuit in the ventilator 11. By way of example, the normal expiratory time in the ventilator 11 can be 30 seconds. When such is the case, the orifice 428 is set for a period of time greater than the 30 seconds.

The reservoirs 431 and 436 are loaded during the inspiratory phase. At the termination of the inspiratory phase, gas will bleed out of the reservoirs 431 and 436 through the orifice 428 at a rate determined by the adjustment of the orifice. In other words, the smaller the size of the orifice, the greater the extended time.

From the foregoing it can be seen that as soon as the I.M.V. Generator master switch 302 is turned on, the ventilator 11 can be required to provide a mandated breath to the patient, which can be delivered on a pressure limiting or a time limiting cycle to deliver the mandated breath. Additional inspiratory delivery is provided by the use of the base line compensator 319.

From the foregoing it can be seen that the I.M.V. Generator complements the functions of the ventilator 11. By delivering additional flow from the demand flow circuit and from the base line compensation, two functions are accomplished. First, during peak spontaneous inspiratory demand (during the maintenance of a positive base line) physiologically induced downward deviation from the base line is minimized, thereby accelerating an inspiratory flow expeditiously as the base line maintenance is depressed. Secondly, inspiratory flow delivered from the ventilator through the nebulizer during the peak demands provides additional saturation of the inspiratory gases. The base line compensator 319 is an automatic pneumatic device capable of being programmed to maintain a specific positive pressure at the proximal airway of the patient. When the proximal airway pressure rises above the programmed value, flow from the base line compensator is retarded. However, more important, as proximal airway pressure is decreased, flow from the base line compensator increases to prevent excessive downward base line deviation. During peak physiological demand, the drop in proximal airway pressure causes self-servoing of the base line compensator 319 as the velocity through the CPAP venturi 369 increases. As the diaphragm 321 of the base line compensator 319 is servoed increasingly open (by the velocity of inspiratory gases flowing past the sensing port 367), the amount of inspiratory demand delivered as complementary gas from the demand flow accelerator circuit is increased to prevent excessive base line deviation while maintaining adequate humidification of inspired gas. By utilizing the expiratory time extension circuit provided in the I.M.V. generator, it is possible to extend the programmed time between the mandated delivery of tidal volumes by the ventilator 11 to an excess of three minute intervals.

From the foregoing it can be seen that the ventilator is of the multi-purpose type and is particularly adapted for direct mechanical ventilation in therapeutic and intensive care applications. In addition, the ventilator can provide servoing capabilities for more sophisticated ventilatory systems. For example, if desired, a safety breathing circuit of the type disclosed in the U.S. Pat. No. 3,812,878 can be provided which has a resuscitory bag built therein. As described in said U.S. Pat. No. 3,812,878, when the ventilator fails for any reason, all that is required is to start squeezing the resuscitation bag to continue the ventilation of the patient.

It should be appreciated that if desired, functions which are performed in the I.M.V. generator cabinet can be transferred to the ventilator cabinet 12. Thus by way of example, the base line compensator 319 can be transferred into the ventilator cabinet 12 and its functions performed therein by using pneumatic plumbing connections which would be obvious to one skilled in the art upon viewing the plumbing connection provided in the ventilator cabinet 12 and the I.M.V. cabinet 77.

It also should be appreciated that in the event certain additional functions are transferred from the I.M.V. generator cabinet 77 into the ventilator cabinet 12, that in many applications it may be possible to eliminate the I.M.V. generator cabinet 77 entirely and to merely utilize the ventilator cabinet 12 to perform the necessary respiratory or ventilator functions.

In place of the over-pressure governor 266 provided on the end member 34 forming the pressure compartment 37, there can be provided an adjustable relief valve assembly 501. This adjustable relief valve assembly 501 has a construction similar to the servoing assembly shown in U.S. Pat. No. 3,753,436. It consists of a two-part housing 502. One part of the housing 502 is bell-shaped member 503 which is provided with a tubular inlet 504 mounted upon a 90 degree elbow 506. The elbow 506 is carried by a one-way check valve 507 mounted in the outlet provided in the end member 34 which the relief valve assembly replaces. Another bell-shaped member 509 forms the other part of the housing 502 and is provided with a cylindrical extension 511. The cylindrical extension is provided with a viewing window 512 used for purpose hereinafter described. The cylindrical extension is also provided with a pair of opposed finger slots 513 also used for a purpose hereinafter described. It is also provided with a pair of additional finger slots 514 also provided for another purpose hereinafter described. The window 516 does not serve a purpose in the present use of the relief valve assembly. The two bell-shaped members of 503 and 509 are adapted to be snapped together and are held together by a retaining ring 518. A flexible diaphragm 521 has its outer margin clamped between the bell shaped members 503 and 509. The central portion of the diaphragm is bonded to a circular disc 522. As is hereinafter described, the disc 522 is secured to a central shaft 523 which is slidably mounted in the cylindrical housing 511 for movement between two extreme positions. As hereinafter described, a plurality of parts are carried by this central shaft and are clamped between two nuts 524 and 526 which have internally threaded sleeves 527 and 528 carried thereby and threaded onto the shaft 523. The upper end of the sleeve 27 engages the lower side of the diaphragm 521 and urges the disc 522 to which the diaphragm 521 is bonded into engagement with a flange 529 carried by sleeve 531 which slidably extends through the bell-shaped member 509. The sleeve 531 has an outer perimeter which is rectangular in cross-section that mates with the rectangular opening 532 provided in the bell shaped member 509 so as to prevent rotation of the central shaft 523 and to only permit rectilinear motion thereof along the axis of the shaft. A pair of externally threaded sleeves 536 and 537 are mounted upon the central shaft 523 and are carried between the upper end of the sleeve 531 and the nut 526. The sleeves 536 and 537 are provided with flanges, portions of which are provided with intermeshing teeth so that the two sleeves 536 and 537 will not rotate with respect to each other. A knurled wheel 541 is threaded onto the sleeve 536 and is adapted to move longitudinally of the central shaft 526 upon rotation of the same by the wheel 541. Similarly, a knurled wheel 542 is threadedly mounted upon the sleeve 537 and also upon rotation is adapted to move longitudinally of the central shaft 523. The knurled wheels of 541 and 542 are formed of a suitable material such as steel which can be attracted by a magnet for a purpose hereinafter described.

Figure 6:
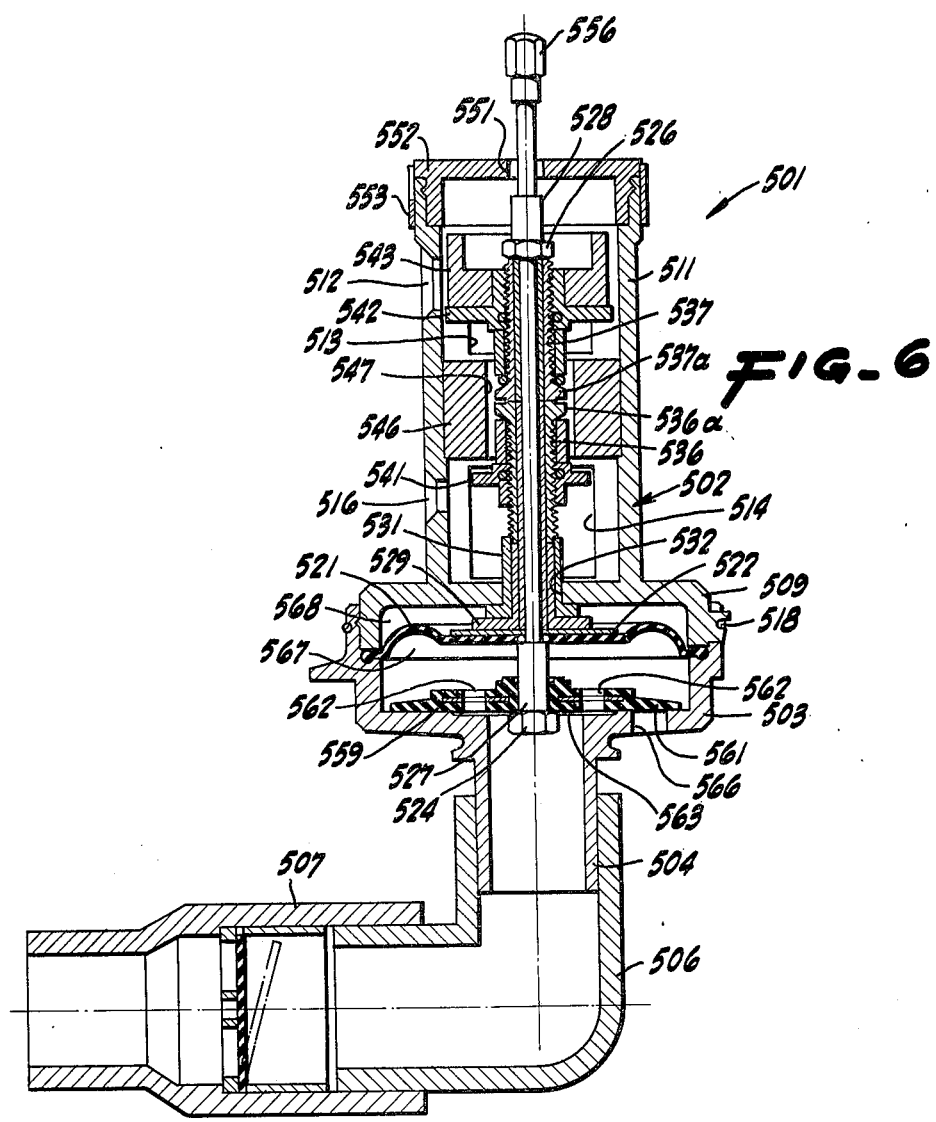
FIG. 6 is a cross-sectional view of the relief valve assembly shown in FIG. 5.
Figure 5:
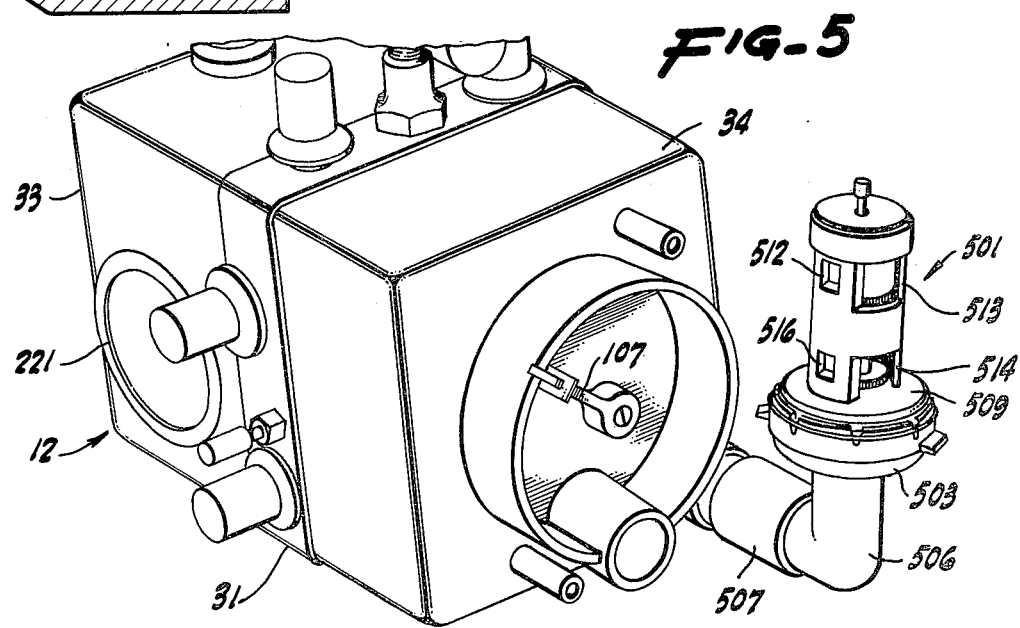
FIG. 5 is a perspective view of a portion of the ventilator incorporating an improved relief valve assembly.

An indicator dial 543 is carried by the knurled wheel 542 and carries indicia which are visible through the window 512 provided in the cylindrical extension 511. A cylindrical magnet 546 is mounted in a suitable manner such as by a press fit within the interior of the cylindrical extension 511 and as can be seen is disposed between the knurled wheels 541 and 542 which serve as armature plates and are attracted by the magnet 546. As can be seen from FIG. 6, the magnet 546 is provided with a centrally disposed hole through which the central shaft 523 and the sleeves 536 and 537 mounted thereon can travel.

The central shaft 523 also extends through a hole 551 provided in an end cap 552 mounted in the upper end of the cylindrical extension 511 and retained therein by a retaining ring 553. The upper end of the central shaft 523 is provided with a knob 556 which can be grasped by the hand so that the central shaft can be moved in an axial direction by hand. A rotor plate 559 is slidably mounted on the sleeve 27 carried by the nut 524 and has bonded thereto a flexible disc-like member 561 formed of a suitable material such as rubber. The disc-like member is provided with a pair of holes 562 which are generally in registration with the recess 563 provided in the bell shaped member 503 and with the interior of the tubular extension 504 so that gas passing through the extensions 504 can pass through the openings or holes 562. The outer margin of the disc-like member 561 is adapted to close a plurality of spaced openings 566 provided in the bell shaped member 503.

Operation of the relief valve assembly may now be briefly described as follows. Let it be assumed that the relief valve assembly has been mounted upon a ventilator of the type described in the present application. In the normal operating position of the relief valve assembly, the central shaft 523 is in its lowermost position with the disc-like member 561 occluding the openings 566. Any gas pressure supplied from the pressure supplied from the pressure compartment 37 through the end member 34 is supplied through the one-way valve 507 through the elbow 506 and into the tubular extension 504 and then through the holes 562 in the rotor plate and into a chamber 567 formed below the diaphragm 521. The chamber 568 in the end bell 509 above the diaphragm 521 is open to the atmosphere through the hole 532 through which the sleeve 531 extends. When a predetermined pressure is reached, the diaphragm 521 is urged upwardly against the pulling forces applied by the magnet 546 applied to knurled wheel 542 which serves as an armature plate. As soon as this movement occurs, the central shaft 523 will snap to its uppermost position because of the attraction of the magnet to the knurled wheel 541. As soon as the central shaft 523 has been moved to its uppermost position, it carries with it the rotor plate 559 and the disc-like member 561 to expose the openings 566 so that gas under pressure can pass from the tubular extension 504 directly to the atmosphere through the openings 566. The knurled wheel 541 which serves as an armature can be adjusted through the finger slots 514 to two extreme positions; one an uppermost position and the other a lowermost position. When the knurled wheel 541 is in the uppermost position, it will be in very close proximity to the magnet 546, and once the rotor plate 559 has been carried to an open position, the central shaft will remain in this position until it is manually closed by engagement of the knob 556. If the knurled wheel 541 is in its lowermost position, it will be spaced sufficiently far from the magnet 546 so that when the overpressure condition is relieved, the attractive forces supplied by the magnet 546 to the upper knurled wheel 542 will cause the central shaft 523 to be moved downwardly to permit the rotor plate 559 with its disc-like member 561 to again move downwardly and occlude the openings 566 provided in the lower bell-shaped member 503. Thus it can be seen by adjustment of the knurled wheel 541, the relief valve can be adjusted so that it will remain in an open position after an overpressure condition is sensed or that it will close as soon as an overpressure condition has been sensed and has been relieved.

The pressure which is required to move the relief valve to the open position is adjusted by movement of the wheel 542 through the finger slots 513. It can be readily appreciated that as the wheel 542 is adjusted so that it is closer to the magnet 546, the attractive forces of the magnet 546 will be greater and the greater the pressure required to open the relief valve. Conversely, the farther it is away from the magnet 546, the less pressure required to open the relief valve. Thus it can be seen there has been provided a relief valve assembly which can be readily adjusted to relieve overpressure conditions and under different pre-selected pressures. The indicator wheel 543 carried by the knurled wheel 542 can be calibrated in centimeters of water pressure as, for example, from 30 to 110 cm. to indicate the various opening pressures for the relief valve assembly. As pointed out previously, these numbers can be seen through the window of 512 provided in the cylindrical extension 511.

What is claimed is:

1. A ventilator providing an inhalation phase and an exhalation phase in its operative cycle comprising a gas inlet line (83) adapted to be coupled to a source of gas under pressure;

a patient adapter (48) having a through opening terminating at an outlet opening adapted to communicate with a patient;

a sequencing switch assembly (94) comprising control valve means (96,99) having an inlet opening (97) coupled to said gas inlet line (83), an outlet opening (98), and a spindle (99) movable between open and closed positions for controlling the flow of gas between said openings (97,98), and control means including means for defining a control chamber including a diaphragm (101) coupled to said spindle (99) for moving said spindle (99) from said closed to said open position in response to gas pressure in said control chamber below a first predetermined pressure and for moving said spindle (99) from said open to said closed position upon gas pressure in said control chamber above a second predetermined pressure which is higher than said first predetermined pressure;

means for connecting the outlet opening (98) of said control valve means with said through opening of said patient adapter (48) to provide a main flow of gas thereto;

means for connecting said control chamber with said through opening of said patient adapter (48) to communicate gas pressures in said through opening with said control chamber so that said spindle (99) will be moved to said open position in response to gas pressure in said through opening below said first predetermined pressure and will be moved to said closed position in response to gas pressure in said through opening above said second predetermined pressure;

exhalation valve means (47) coupled to the through opening of said patient adapter (48), having an operating chamber, and having a portion (377) movable from a normal open position permitting gas flow to the atmosphere from the patient adapter to a closed position preventing gas flow to the atmosphere from the patient adapter when the gas pressure in said operating chamber is above a third predetermined pressure;

conduit means (52,53,54) for directing a secondary flow of gas at above said third predetermined pressure to said patient adapter (48) and to the operating chamber of said exhalation valve means (47);

apneustic hold means (91) having an inlet line (90) coupled to said gas inlet line (83) and an outlet line (238) and including means for supplying gas from said inlet line (90) to said outlet line (238) while said spindle (99) is in said open position and for a predetermined time after said spindle (99) is moved from said open position to said closed position;

mode selector means (161) including first and second inlets and an outlet, means connecting the outlet opening (98) of said control valve means to said first inlet of said mode selector means, means connecting the outlet line (238) of said apneustic hold means to the second inlet of said mode selector means, means connecting the outlet of said mode selector means to said conduit means, said mode selector means including a portion (162,163,164) manually movable between a first position for connecting the first inlet of aid mode selector means to its outlet, and a second position connecting its second inlet to its outlet whereby, when said portion (162,163,164) is positioned in its first position, gas is directed to said patient adapter (48) and said exhalation valve means (47) from the outlet opening (98) of said control valve means via said conduit means (52,53,54) only when said spindle (99) is in said open position; and when said portion (162,163,164) is positioned in its second position gas is directed to said patient adapter (48) and said exhalation valve means (47) from said gas inlet line (83) via said apneustic hold means (91) and said conduit means (52,53,54) when said spindle (99) is in its open position and for a predetermined time after said spindle (99) moves to its closed position.

2. A ventilator according to claim 1 wherein said means for connecting said control chamber with the through opening of said patient adapter (48) comprises a sensing/servoing venturi having an outlet opening (213) communicating with the inlet opening of said patient adapter (48), a throat (226) communicating with said control chamber and an inlet (224); and said ventilator further includes timing means (86) coupled to said gas inlet line (83) for applying gas under pressure through the inlet (224) of said sensing/servoing venturi to thereby reduce the gas pressure in said control chamber below said first predetermined pressure and move said spindle (99) to its open position a predetermined time after gas pressure is relieved in said control line (54) for said exhalation valve means (47) if gas pressure in said control chamber is not previously reduced below said first predetermined pressure by inhalation of a said patient through said patient adapter (48).

3. A ventilator according to claim 1 wherein said means for connecting the outlet opening (98) of said control valve means (96,99) with the through opening of said patient adapter (48) includes a master venturi (128) having an outlet communicating with the opening through said patient adapter (48), an inlet (157) communicating with the outlet opening (98) of said control valve means (96, 99) and a throat; and said ventilator further includes means for supplying intermittent mandatory ventilation (76) including IMV switch means (302) having an inlet line (301) coupled to said gas inlet line (83), and an outlet line (304); demand flow accelerator mwans (308) for supplying gas to the patient adapter (48) for voluntary inhalation by the patient between intermittent mandatory ventilations, said demand flow accelerator means (308) having an inlet line (309) coupled to the outlet line (304) of said IMV switch means (302), an outlet line (413), a control line and means (311, 312) for opening a passageway between its inlet and outlet lines (309, 413) in response to a reduced gas pressure in its control line; means coupling the outlet line (413) of the demand flow accelerator means (308) to the inlet (157) of the master venturi (128); and means (366) coupling the control line of the demand flow accelerator means (308) to the opening through said patient adapter (48) so that a reduction in pressure in the patient adapter (48) caused by inhalation by the patient between mandatory ventilation will operate said demand flow accelerator means (308) and supply gas to the patient for voluntary inhalation.

4. A ventilator according to claim 3 wherein said ventilator further includes base line compensator means (319) for maintaining a predetermined pressure against which a patient to which the patient adapter (48) is coupled must exhale, said base line compensator means (319) having an inlet line (318) coupled to the outlet line (304) of said IMV switch means (302), an outlet line (417), a control line (362) and means (321, 322) for opening a passageway between its inlet and outlet lines (318, 417) in response to a reduced gas pressure in its control line (362); means for coupling the outlet line (417) of the base line compensator means (319) to the inlet (157) of the master venturi (128); and (366) for connecting the control line (362) of the base line compensator means (319) to the opening through the patient adapter (48) so that when there is a reduction in the gas pressure in the opening through the patient adapter (48) below a predetermined pressure determined by the base line compensator means (319), gas will be supplied through the IMV switch means (302) and the master venturi (128) to the patient adapter (48).

5. A ventilator according to claim 1 further including a relief valve assembly (501) coupled to said means for connecting the outlet opening (98) of said control valve means (96, 99) with the through opening of said patient adapter (48) said relief valve assembly (501) comprising a housing including first and second portions defining a chamber, said first portion having an inlet opening communicating with said means for connecting the outlet opening (98) of said control valve means (96, 99) with the through opening of said patient adapter (48) and an outlet opening (566) to the atmosphere from said chamber through said first portion, a second portion having an outlet opening (532) to the atmosphere from said chamber through said second portion; a flexible diaphragm (521) between said housing portions dividing said chamber into first and second chamber portions (567, 568); a shaft (523) fixed to said diaphragm (521) and slidably mounted in said housing through said chamber portions (567, 568) a blocking member (561) mounted on said shaft (523) in said first chamber portion (567) to move with said shaft from a position closing said outlet opening (566) in said first chamber portion (567) to a position spaced from said outlet opening (566) and means for applying a predetermined adjustable magnetic force to hold said blocking member (561) in its position closing the outlet opening (566) in said first position in opposition to gas pressure against said diaphragm (521) in said first chamber portion (567).

* * * * *